United States Patent [19]
Lurie et al.

[11] Patent Number: 5,551,420
[45] Date of Patent: Sep. 3, 1996

[54] CPR DEVICE AND METHOD WITH STRUCTURE FOR INCREASING THE DURATION AND MAGNITUDE OF NEGATIVE INTRATHORACIC PRESSURES

[75] Inventors: Keith G. Lurie, Minneapolis; Michael Sweeney, St. Paul; Barbara Gold, Minneapolis, all of Minn.

[73] Assignee: CPRx, Inc., Minneapolis, Minn.

[21] Appl. No.: 149,204

[22] Filed: Nov. 9, 1993

[51] Int. Cl.⁶ .................................. A62B 9/02; A62B 7/00
[52] U.S. Cl. ................................. 128/205.13; 128/205.24; 128/207.15; 128/207.16
[58] Field of Search .................... 128/205.13, 205.19, 128/207.15, 207.16, 911, 912, 202.28–203.11, 204.18, 205.13–205.16, 205.24, 207.14–207.16

[56] References Cited

U.S. PATENT DOCUMENTS

| | | | |
|---|---|---|---|
| 4,166,458 | 9/1979 | Harrigan | 128/30.2 |
| 4,316,458 | 2/1982 | Hammerton-Fraser | 128/207.15 |
| 4,446,864 | 5/1984 | Watson et al. | 128/207.14 |
| 4,449,526 | 5/1984 | Elam | 128/207.14 |
| 4,601,465 | 7/1986 | Roy | 272/99 |
| 4,881,527 | 11/1989 | Lerman | 128/30.2 |
| 5,109,840 | 5/1992 | Daleiden | 128/205.13 |
| 5,163,424 | 11/1992 | Kohnke | 128/205 |
| 5,193,544 | 3/1993 | Jaffe | 128/634 |
| 5,235,970 | 8/1993 | Augustine | 128/200 |
| 5,301,667 | 4/1994 | McGrail et al. | 128/205.13 |

FOREIGN PATENT DOCUMENTS

| | | | |
|---|---|---|---|
| 0509773 | 10/1992 | European Pat. Off. | |
| 2139099 | 11/1984 | United Kingdom | 128/205.13 |

OTHER PUBLICATIONS

Directions for use Ambu® CardioPump™, pp. 1–8.
Cohen et al. (1992) "Active Compression–Decompression Resuscitation: a Novel Method of Cardiopulmonary Resuscitation" *American Heart Journal* 126(5):1145–1150.
Cohen et al. (1992) "Active Compression–Decompression: A New Method of Cardiopulmonary Resuscitation" *JAMA* 267(21):2916–2923.
Lindner et al. (1993) "Effects of Active Compression–Decompression Resuscitation on Myocardial and Cerebral Blood Flow in Pigs" *Circulation* 88(3):1254–1263.

*Primary Examiner*—Kimberly L. Asher
*Attorney, Agent, or Firm*—Townsend and Townsend and Crew LLP

[57] ABSTRACT

According to the invention, methods and devices for increasing cardiopulmonary circulation induced by chest compression and decompression when performing cardiopulmonary resuscitation are provided. Cardiopulmonary circulation is increased according to the invention by impeding air flow into a patient's lungs to enhance the extent and duration of negative intrathoracic pressure during decompression of the patient's chest. Enhanced extent and duration of negative of intrathoracic pressure thus promotes venous blood flow into the heart and lungs from the peripheral venous vasculature. In one embodiment, impeding the air flow into the patient's lungs is accomplished by placing a ventilation tube in the patient's airway. The ventilation tube contains either a flow restrictive orifice disposed within or connected in series with a lumen of the ventilation tube, or a pressure-responsive valve within a lumen of the tube to impede the inflow of air. In a preferred embodiment, the patient's mouth and nose are covered with a facial mask which can impede air flow into the patient's airway. Also provided is an improved endotracheal tube to allow air to be impeded from flowing to the patient's lungs during decompression. Another apparatus according to the invention provides for an improved air-delivery system comprising a compressible structure which has been modified to allow for the impedance of the flow of gases to the patient's lungs. Also, the compressible structure is interfaced with the patient, preferably by attaching a facial mask or an endotracheal to the structure.

41 Claims, 5 Drawing Sheets

CPR DEVICE AND METHOD WITH STRUCTURE FOR INCREASING THE DURATION AND MAGNITUDE OF NEGATIVE INTRATHORACIC PRESSURES

BACKGROUND OF THE INVENTION

1. Field of the Invention

The present invention relates generally to devices and methods used in conjunction with external chest compression and decompression as a part of cardiopulmonary resuscitation procedures. In particular, the present invention relates to devices and methods for increasing cardiopulmonary circulation induced by chest compression and decompression when performing cardiopulmonary resuscitation.

Worldwide, sudden cardiac arrest is a major cause of death and is the result of a variety of circumstances, including heart disease and significant trauma. In the event of a cardiac arrest, several measures have been deemed to be essential in order to improve a patient's chance of survival. These measures must be taken as soon as possible to at least partially restore the patient's respiration and blood circulation. One common technique, developed approximately 30 years ago, is an external chest compression technique generally referred to as cardiopulmonary resuscitation (CPR). CPR techniques have remained largely unchanged over the past two decades.

With traditional CPR, pressure is applied to a patient's chest in order to increase intrathoracic pressure. An increase in intrathoracic pressure induces blood movement from the region of the heart and lungs towards the peripheral arteries. Such pressure partially restores the patient's circulation. Traditional CPR is performed by actively compressing the chest by direct application of an external pressure to the chest. After active compression, the chest is allowed to expand by its natural elasticity which causes expansion of the patient's chest wall. This expansion allows some blood to enter the cardiac chambers of the heart. The procedure as described, however, is insufficient to ventilate the patient. Consequently, conventional CPR also requires periodic ventilation of the patient. This is commonly accomplished by mouth-to-mouth technique or by using positive-pressure devices, such as a self-inflating bag which relies on squeezing an elastic bag to deliver air via a mask, endotracheal tube or other artificial airway.

In order to increase cardiopulmonary circulation induced by chest compression, a technique referred to as active compression-decompression (ACD) has been developed. According to ACD techniques, the active compression phase of traditional CPR is enhanced by pressing an applicator body against the patient's chest to compress the chest. Such an applicator body is able to distribute and apply force substantially evenly over a portion of the patient's chest. More importantly, however, the applicator body is sealed against the patient's chest so that it may be lifted to actively expand the patient's chest during the decompression step. The resultant negative intrathoracic pressure induces venous blood to flow into the heart and lungs from the peripheral venous vasculature of the patient.

Also of importance to the invention are ventilation sources that are used in connection with CPR techniques to properly ventilate the patient. One type of ventilation source is the AMBU bag available from AMBU International, Copenhagen, Denmark. The AMBU bag can also be used in connection with a positive end-expiratory pressure (PEEP) valve, available from AMBU International, to treat some patients with pulmonary and cardiac diseases.

With both traditional CPR and ACD-CPR techniques, an increase in the amount of venous blood flowing into the heart and lungs from the peripheral venous vasculature would be desirable to increase the volume of oxygenated blood leaving the thorax during the subsequent compression phase. It would therefore be desirable to provide improved methods and apparatus for enhancing venous blood flow into the heart and lungs of a patient from the peripheral venous vasculature during both conventional CPR and ACD-CPR techniques. It would be particularly desirable to provide techniques which would enhance oxygenation and increase the total blood return to the chest during the decompression step of CPR and ACD-CPR, more particularly of ACD-CPR. This can be accomplished according to the present invention by augmentation of both negative and positive intrathoracic pressure, thereby amplifying the total intrathoracic pressure swing. An invention for providing this crucial improvement is described.

2. Description of the Background Art

ACD-CPR techniques are described in detail in Todd J. Cohen et al., *Active Compression-Decompression Resuscitation: A Novel Method of Cardiopulmonary Resuscitation*, American Heart Journal, Vol. 124, No. 5, pp. 1145–1150, November 1992; Todd J. Cohen et al., *Active Compression-Decompression: A New Method of Cardiopulmonary Resuscitation*, The Journal of the American Medical Association, Vol. 267, No. 21, Jun. 3, 1992; and These references are hereby incorporated by reference.

The use of a vacuum-type cup for actively compressing and decompressing a patient's chest during ACD-CPR is described in a brochure of AMBU International A/S, Copenhagen, Denmark, entitled Directions for Use of AMBU® CardioPump™, published in September 1992. The AMBU® CardioPump™ is also disclosed in European Patent Application No. 0 509 773 A1. These references are hereby incorporated by reference.

SUMMARY OF THE INVENTION

According to the invention, methods and devices for increasing cardiopulmonary circulation induced by chest compression and decompression when performing cardiopulmonary resuscitation are provided. The methods and devices may be used in connection with any generally accepted CPR methods or with active compression-decompression (ACD) CPR techniques. Preferably, the methods and devices will be used in connection with ACD-CPR.

Cardiopulmonary circulation is increased according to the invention by impeding air flow into a patient's lungs during the decompression phase. This increases the magnitude and prolongs the duration of negative intrathoracic pressure during decompression of the patient's chest, i.e., increases the duration and degree that the intrathoracic pressure is below or negative with respect to the pressure in the peripheral venous vasculature. By enhancing the amount of venous blood flow into the heart and lungs, since equilibration of intrathoracic pressure during decompression occurs to a greater extent from enhanced venous return rather than rapid inflow of gases into the chest via the patient's airway, cardiopulmonary circulation is increased. In one particular aspect, the invention provides a method for impeding air flow into the patient's lungs with an inflow impeding means for impeding inflow without substantially impeding outflow.

In a specific embodiment, impeding the air flow into the patient's lungs is accomplished by decreasing or preventing ventilation during the decompression phase of CPR. The method employs the use of a flow restrictive or limiting member, such as a flow restrictive orifice disposed within or connected in series with a lumen of a ventilation tube, or a pressure-responsive valve within a lumen of the tube to impede the inflow of air. The pressure-responsive valve is biased to open to permit the inflow of air when the intrathoracic pressure falls below a threshold level. In order to properly ventilate the patient, the method preferably provides for periodically ventilating the patient through the ventilation tube after compression of the patient's chest. When periodic ventilation is performed, gases can be delivered either through the impeding step or in another embodiment they can bypass the impeding step.

An exemplary embodiment provides for covering the patient's mouth and nose with a facial mask. This mask contains means for impeding air flow into the patient's airway during decompression of the patient's chest, e.g. either an orifice or valve as just discussed.

A specific embodiment further provides means for impeding air from leaving the lungs during compression of the patient's chest to further enhance cardiopulmonary circulation by enhancing positive intrathoracic pressure during the compression phase.

When performing cardiopulmonary resuscitation to enhance circulation according to the invention, an operator compresses a patient's chest to force blood out of the patient's thorax. The patient's chest is then decompressed to induce venous blood to flow into the heart and lungs from the peripheral venous vasculature either by actively lifting the chest (via ACD-CPR) or by permitting the chest to expand due to its own elasticity (via conventional CPR). During the decompression step, air flow is impeded from entering into the patient's lungs which enhances negative intrathoracic pressure and increases the time during which the thorax is at a lower pressure than the peripheral venous vasculature. Thus, venous blood flow into the heart and lungs from the peripheral venous vasculature is enhanced. This is because the intrathoracic pressure equilibrium during decompression occurs as a result of enhanced venous return rather than from inflow of air via the trachea. In a particular embodiment, compression and decompression of the patient's chest may be accomplished by pressing an applicator body against the patient's chest to compress the chest, and lifting the applicator to actively expand the patient's chest.

An apparatus for enhancing cardiopulmonary circulation according to the method comprises an improved endotracheal tube having a flow restrictive element for impeding air flow from the patient's lungs during chest decompression. A second apparatus according to the invention provides for an improved air-delivery system comprising a compressible structure having a flow restrictive element included in or attached to an opening of the compressible structure to impede the flow of gases to the patient's lungs. Also, a connector is provided for interfacing the compressible structure to the patient, preferably by attaching a facial mask or endotracheal tube to the structure.

A further understanding of the nature and advantages of the invention will become apparent by reference to the remaining portions of the specification and drawings.

DETAILED DESCRIPTION OF SPECIFIC EMBODIMENTS

According to the present invention, methods and devices for increasing cardiopulmonary circulation induced by chest compression and decompression when performing cardiopulmonary resuscitation are provided. Such methods and devices may be used in connection with any method of CPR in which intrathoracic pressures are intentionally manipulated to improve cardiopulmonary circulation. For instance, the present invention would improve standard manual CPR, "vest" CPR, CPR with a newly described Hiack Oscillator ventilatory system which operates essentially like an iron-lung-like device, interposed abdominal compression-decompression CPR, and active compression-decompression (ACD) CPR techniques. Although the present invention may improve all such techniques, the following description will refer primarily to improvements of ACD-CPR techniques in order to simplify discussion. However, the claimed methods and devices are not exclusively limited to ACD-CPR techniques.

The proper performance of ACD-CPR to increase cardiopulmonary circulation is accomplished by actively compressing a patient's chest with an applicator body. Preferably, this applicator body will be a suction-type device that will adhere to the patient's chest, such as the AMBU® CardioPump™, available from AMBU International, Copenhagen, Denmark. After the compression step, the adherence of the applicator body to the patient's chest allows the patient's chest to be lifted to actively decompress the patient's chest. The result of such active compression-decompression is to increase intrathoracic pressure during the compression step, and to increase the negative intrathoracic pressure during the decompression step thus enhancing the blood-oxygenation process and enhancing cardiopulmonary circulation. ACD-CPR techniques are described in detail in Todd J. Cohen et al., *Active Compression-Decompression Resuscitation: A Novel Method of Cardiopulmonary Resuscitation*, American Heart Journal, Vol. 124, No. 5, pp. 1145-1150, November 1992; Todd J. Cohen et al., *Active Compression-Decompression: A New Method of Cardiopulmonary Resuscitation*, The Journal of the American Medical Association, Vol. 267, No. 21, Jun. 3, 1992; and J. Schultz, P. Coffeen, et al., Circulation, in press, 1994. These references are hereby incorporated by reference.

The present invention is especially useful in connection with ACD-CPR techniques. In particular, the invention improves ACD-CPR by providing methods and devices which impede air flow into a patient's lungs to enhance negative intrathoracic pressure during the decompression of the patient's chest, thus increasing the degree and duration of a pressure differential between the thorax (including the heart and lungs) and the peripheral venous vasculature. Enhancing negative intrathoracic pressure with simultaneous impedance of movement of gases into the airway thus enhances venous blood flow into the heart and lungs and increases cardiopulmonary circulation.

In a broad sense, the present invention provides for occluding a patient's airway to prevent foreign (outside) air from flowing to a patient's lungs during the active decompression step of ACD-CPR to enhance and sustain the duration of negative intrathoracic pressure and enhance blood oxygenation and cardiopulmonary circulation during both active decompression and the subsequent compression phase. The patient's airway may be occluded or inflow of gases impeded by any suitable device or mechanism such as by an endotracheal tube, a device attached to an endotracheal tube, a facial mask, a mouth piece used in mouth-to-mouth resuscitation, oropharyngeal airway, laryngeal mask airway, and the like.

A further aspect of the present invention provides for allowing impeded air to flow into the patient's lungs during the active decompression step of ACD-CPR in order to provide some ventilation to the patient while still enhancing the extent and duration of negative intrathoracic pressure to enhance blood oxygenation. Impeding air flow to the patient's lungs may be accomplished by any flow restrictive element such as an orifice, a spring biased or other valve which is set to open when the negative intrathoracic pressure is in the range from about 0 cm $H_2O$ to $-100$ cm $H_2O$, a one-way valve, or the like. A valve designed to open at a threshold pressure value may be either fixed or variable, i.e., the pressure at which the valve opens may be adjusted or may be permanently fixed.

Similarly, another aspect of the invention provides for air to be impeded from leaving the patient's lungs during compression of the patient's chest to further enhance cardiopulmonary circulation by enhancing intrathoracic pressure during the compression phase. Typically, air is impeded from leaving the lungs during the compression phase when the positive intrathoracic pressure is in the range from about 5 cm $H_2O$ to 50 cm $H_2O$.

Another aspect of the present invention provides for ventilating the patient during ACD-CPR. Ventilation of the patient is performed at about every two to 10 compressions, preferably every five compressions, thus providing sufficient fresh air for adequate gas exchange with the blood in the lungs to the patient. Ventilating the patient may be accomplished by any device or method suitable such as by mouth-to-mouth resuscitation, by a compressible or collapsible structure, by a ventilatory bag such as the AMBU bag available from AMBU, Copenhagen, Denmark, or the like. Ventilation could also be superimposed on the compression phase to further augment positive intrathoracic pressure. Furthermore, periodic ventilation could be performed either through the impeding step or by bypassing the impeding step altogether.

Figure 1:
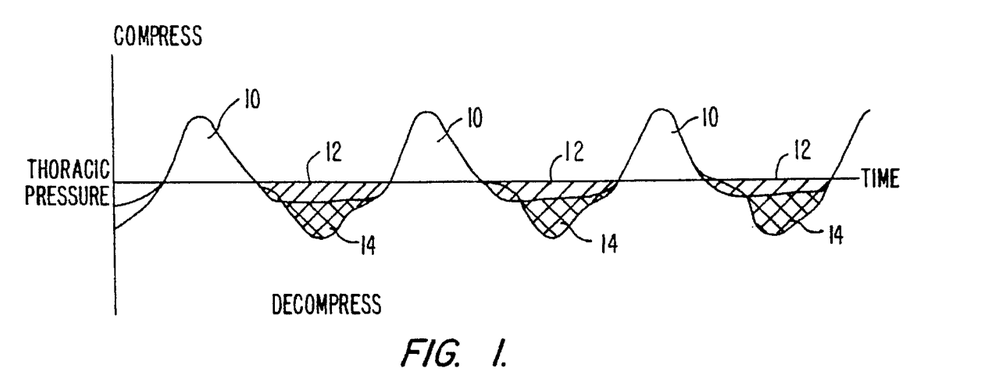
FIG. 1 is a graph illustrating thoracic pressure changes over time when compressing and decompressing a patient's chest according to the present invention.

Referring now to FIG. 1, a graph illustrating thoracic pressure changes over time when compressing and decompressing the patient's chest is shown. Area 10 represents the amount of thoracic pressure during the compression phase of ACD-CPR. Cross-hatched area 12 represents the negative thoracic pressure during the decompression step of ACD-CPR without a flow restrictive means to restrict the flow of air into the patient's lungs. Double cross-hatched area 14 represents the increase in negative thoracic pressure when the patient's airway is occluded according to the present invention during the decompression step of ACD-CPR. The significance of the increase in negative intrathoracic pressure during the decompression step is that more venous blood is forced into the chest from the peripheral venous vasculature. Consequently, more blood is allowed to be oxygenated and more blood is forced out of the chest during the next compression.

In an exemplary embodiment, air flow may be impeded to the patient's lungs during decompression of the patient's chest by placing a ventilatory mask over the patient's mouth and nose. The ventilatory mask also has a pressure-responsive valve attached to prevent air flow to the patient's lungs until the negative intrathoracic pressure of the patient reaches a threshold amount. Also attached to the mask and the pressure-responsive valve is a ventilatory source to provide ventilation to the patient. The ventilatory source may be any device or apparatus suitable for properly ventilating the patient. Preferably, the ventilation source will be an AMBU bag. When ventilation is needed, the AMBU bag may be squeezed to force air into the patient's lungs. The AMBU bag is described in U.S. Pat. No. 5,163,424 which is incorporated herein by reference.

In an alternative embodiment, a ventilation source, preferably an AMBU bag, is used in connection with an improved endotracheal tube. A pressure-responsive valve or other flow restrictive element is placed between the AMBU bag and the endotracheal tube. Preferably, the valve will be positioned within a tube that connects the AMBU bag to the endotracheal tube. The combination of the endotracheal tube with the AMBU bag with adapter can be included in the definition of a "ventilation tube." Before ACD-CPR is performed on the patient, the endotracheal tube is placed in the patient's trachea. During decompression of the patient's chest, the valve prevents air flow to the patient's lungs until the intrathoracic pressure reaches a threshold amount. Additionally, the AMBU bag may be used to ventilate the patient at a desired time. Also included in this embodiment is a one-way expiration valve. This valve allows for expiration of air from the patient during the compression step.

In a modification of either of the first two embodiments, pressure-responsive expiration valve may also be inserted between the AMBU bag (or comparable ventilation source) and the mask or endotracheal tube. This valve works in a similar manner to the pressure-responsive valve which restricts air flow into the patient's lungs. However, the pressure-responsive expiration valve restricts air flow from the patient's lungs during the compression step of ACD-CPR. An equivalent valve is a positive end-expiratory pressure (PEEP) valve available from AMBU International, Copenhagen, Denmark. Use of such pressure-responsive expiration valve during compression may further increase intrathoracic pressure and thereby force more blood out of the thorax.

In another alternative embodiment, an improved endotracheal tube is used to restrict air flow into the patient's lungs during the active decompression step. Included in the endotracheal tube is a flow restrictive element which operates to impede air from flowing into the patient's lungs. When the endotracheal tube is inserted into the patient's trachea and the patient's chest is actively decompressed, the flow restrictive element impedes air from flowing to the patient's lungs slowing the rise in intrathoracic pressure and thus enhancing blood oxygenation.

When using the improved endotracheal tube during ACD-CPR, periodic ventilation of the patient will usually still be performed to enhance gas exchange to the patient. With the improved endotracheal tube, such manual ventilation may be accomplished by placing a ventilation source at the opening of the endotracheal tube to force oxygen through the endotracheal tube and into the patient's lungs.

Figure 2A:
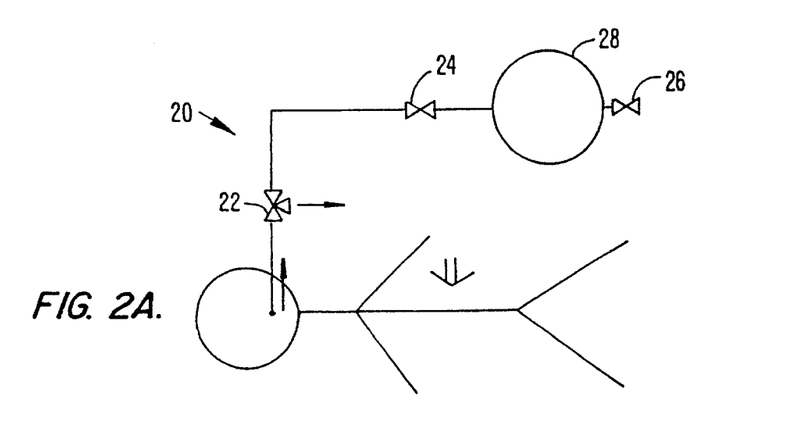
FIG. 2A is a schematic view illustrating air flow through a ventilation circuit when compressing a patient's chest according to the present invention.

Referring now to FIG. 2A, a schematic view illustrating air flow through a ventilation circuit 20 when compressing a patient's chest according to the present invention is shown. During ACD-CPR, the chest is actively compressed forcing air out of the lungs. This air is allowed to expire through a one-way expiration valve 22 within a ventilation circuit 20.

Figure 2B:
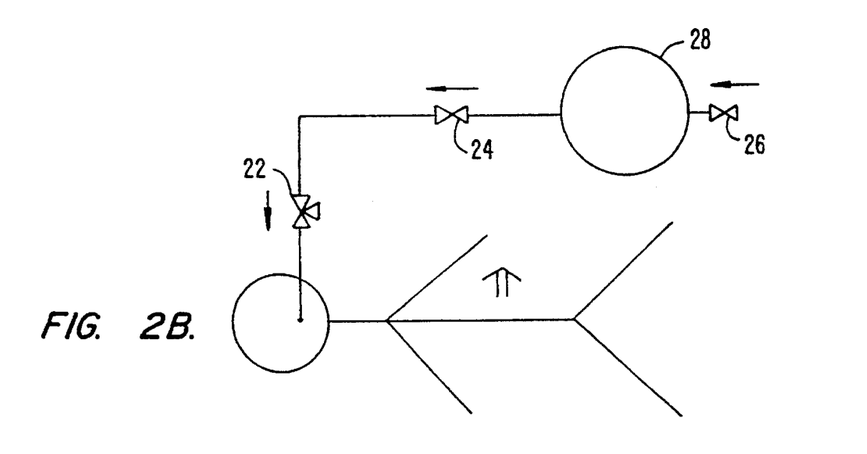
FIG. 2B is a schematic view illustrating air flow through a ventilation circuit when decompressing a patient's chest according to the present invention.

Referring now to FIG. 2B, the same schematic is shown illustrating air flow through the ventilation circuit 20 when decompressing the patient's chest. When the patient's chest is actively decompressed, a negative intrathoracic pressure is created. When this pressure reaches a threshold amount, the inflow valve 24 will open causing air to flow through the ventilation circuit 20 into the patient's lungs. Air is allowed into the ventilation circuit 20 through a ventilation valve 26 and into a ventilation bag 28. From the ventilation bag 28, the air passes through the inflow valve 24 when the negative intrathoracic pressure reaches the threshold amount. The ventilation bag 28 is also used to manually ventilate the patient during ACD-CPR as required.

The method as discussed in connection with FIGS. 2A and 2B requires the chest to be compressed in the range from about 3.5 cm to 5 cm per compression and at a rate from about 60 to 100 compressions per minute for adults.

Figure 3:
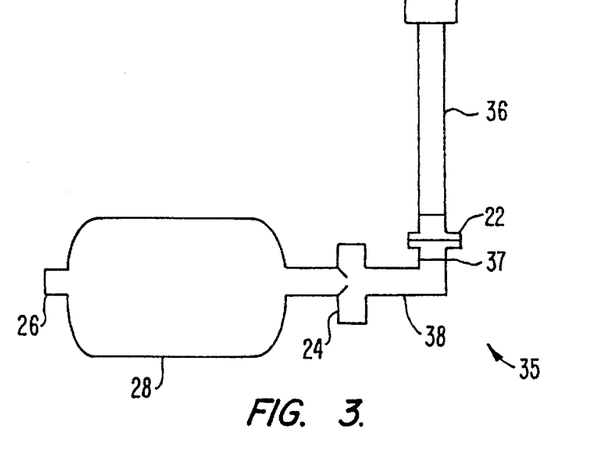
FIG. 3 is a schematic illustration of a first alternative embodiment of a device for impeding air flow into a patient's lungs according to the present invention.

Referring now to FIG. 3, a schematic illustration of a first alternative embodiment of a device 35 for impeding air flow into a patient's lungs according to the present invention is shown. The device 35 comprises an endotracheal tube 36 which is placed into the patient's trachea and provides a ventilation passageway. Connected to the endotracheal tube 36 is a transition tube 38 which connects the endotracheal tube 36 to the ventilation bag 28. Although the endotracheal tube 36 is shown connected to the ventilation bag 28, the endotracheal tube 36 can be used alone or in connection with the ventilation bag 28. The ventilation bag 28 can comprise any type of ventilation source capable of ventilating the patient such as a compressible or collapsible structure. Preferably, the ventilation bag 28 consists of an AMBU bag. Attached or connected to the end of the ventilation bag 28 is a one-way ventilation valve 26. The ventilation valve 26 serves to introduce air into the device 35. Attached or connected to the transition tube 38 is an inflow pressure-responsive valve 24. The inflow valve 24 is biased so that it opens when the negative intrathoracic pressure in the patient's chest reaches a threshold amount. As shown, only one inflow valve 24 is included in the device 35. However, the invention is not limited to only one inflow valve 24. Alternatively, a plurality of inflow valves 24 could be connected in series along the ventilation tube 38. The inflow valve 24 is also not limited to being connected in the center of the transition tube 38, but may be positioned anywhere along the transition tube 38. The inflow valve 24 could be permanently attached to the ventilation bag 28 or transition tube 38 or could be detachable. Alternatively, the inflow valve 24 could be connected to the ventilation bag 28 itself or to the endotracheal tube 36.

The device 35 also contains a one-way expiration valve 22 which allows for air to be expired from the patient's lungs. This generally occurs during the compression phase of ACD-CPR. To insure that the air expired from the patient's lungs will exit through the expiration valve 22, a one-way fish mouth valve 37 (the preferred valve) or any other type of one-way valve can be placed between the inflow valve 24 and the expiration valve 22. Alternatively, the inflow valve 24 itself may be configured as a one-way valve. In either case, air flowing from the endotracheal tube 36 toward the ventilation bag 28 will be forced to expire through the expiration valve 22.

The device 35 may be further modified to include a pressure-responsive expiration valve 39 (not shown) located between the endotracheal tube 36 and the transition tube 38. The pressure-responsive expiration valve works in a reverse manner to that of the inflow valve 24. Specifically, the pressure-responsive expiration valve is biased so that during the compression step of ACD-CPR, air will be allowed to expire from the patient's lungs only when the intrathoracic pressure reaches a threshold amount. The increase in intrathoracic pressure caused by the pressure-responsive expiration valve 39 during compression may assist in forcing more blood out of the thorax and reduce atelectasis of the lungs.

The purpose of the ventilation bag 28 is to provide ventilation to the patient during ACD-CPR. When the ventilation bag 28 comprises an AMBU bag or similar bag used for ventilation, ventilation of the patient may be performed by merely squeezing the AMBU bag with a human hand. This forces air to the patient's lungs as desired.

Figure 4A:
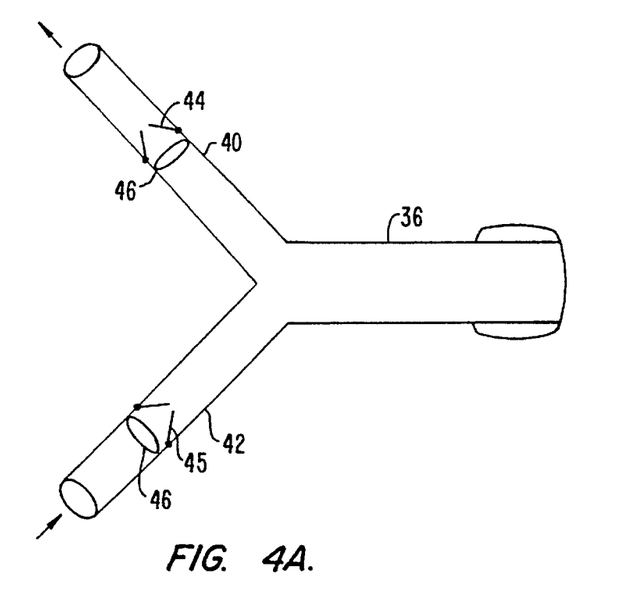
FIG. 4A is a schematic illustration of a second alternative embodiment of the device for impeding air flow into a patient's lungs according to the present invention.

Referring to FIG. 4A, a second alternative embodiment of the device for impeding air flow into a patient's lungs according to the present invention is shown. This particular embodiment is a modified and improved endotracheal tube. Hence, the second alternative embodiment comprises an endotracheal tube 36 having two lumens at its proximal end. The first lumen is an outflow lumen 40, and the second lumen is an inflow lumen 42. Located within outflow lumen 40 is a one-way pressure-responsive expiration valve 44 which operates in a manner similar to that discussed in connection with FIG. 3, except that the expiration valve 44 is specifically designed as a one-way valve. Located within inflow lumen 42 is a one-way pressure-responsive inflow valve 45 which operates to impede air flow to the lungs as discussed in connection with FIG. 3, except that the inflow valve 45 is also specifically designed as a one-way valve.

Also shown in inflow lumen 42 and outflow lumen 40 is an O-ring 46 which will be discussed subsequently. Inflow valve 45 and expiration valve 44 are designed as one-way valves so that during the compression phase, air can only be expired from the patient through the endotracheal tube 36 when the intrathoracic pressure reaches a threshold amount. At that moment, expiration valve 44 opens and air expires from the patient through the outflow lumen 40. During decompression, air cannot flow through the endotracheal tube 36 to the patient's lungs until the negative intrathoracic pressure reaches a threshold amount. At that moment, inflow valve 45 opens allowing air to flow through inflow lumen 42 to the patient's lungs. Air is prevented from entering through the outflow lumen 40 because of the one-way expiration valve 44.

Figure 4B:
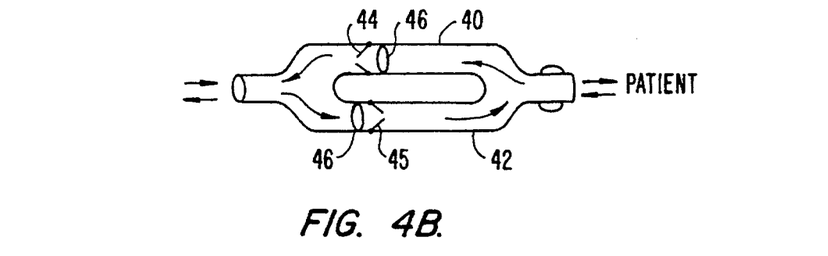
FIG. 4B is a schematic illustration of the device in FIG. 4A with a common inhalation/exhalation port.

Ventilation is possible with the embodiment disclosed in FIGS. 4A and 4B if the inflow lumen 42 is connected to a ventilation source such as a ventilation bag. When the ventilation bag is squeezed, air is allowed to flow through the inflow lumen 42, through the endotracheal tube 36, and to the patient's lungs. In this embodiment, expiration valve 44 is designed so that during ventilation, expiration valve 44 will remain temporarily closed preventing air flowing through inflow lumen 42 escape through outflow lumen 40.

Figure 5A:
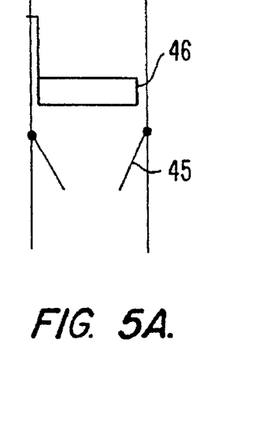
FIG. 5A is a schematic view of a one-way valve used in the device for impeding air flow according to the present invention.
Figure 5B:
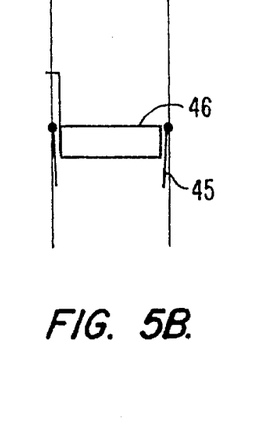
FIG. 5B is a schematic view of the one-way valve in FIG. 5A that is held open after ACD-CPR has ceased.
Figure 5C:
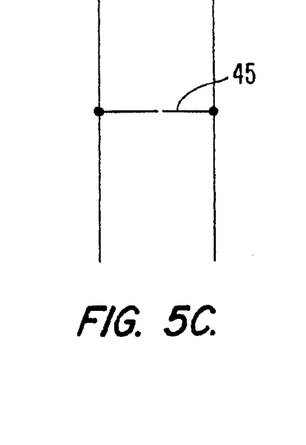
FIG. 5C is a schematic view of a one-way valve that is closed until a threshold pressure is present in the tube according to the present invention.

FIG. 5A is a schematic view of a one-way inflow valve 45 used in a device for impeding air flow according to the present invention. The inflow valve 45 operates so as to allow air only to flow in one direction. As shown, the spring biased inflow valve 45 is completely open. However, the invention also functions properly if the spring biased inflow valve 45 or the spring biased expiration valve 44 are not fully open. Upon successful completion of ACD-CPR, the o-ring 46 that is positioned above the inflow valve 45 is repositioned so that inflow valve 45 is held open as shown in FIG. 5B. Such a positioning of O-ring 46 allows for unimpeded air flow to the patient once there is a return of spontaneous circulation and the inflow valve 45 is no longer needed. An O-ring 46 is also used in a similar manner to lock the one-way expiration valve 44 in an open position upon return of spontaneous circulation. FIG. 5C illustrates the one-way inflow valve 45 in a closed position. When closed, the inflow of air through the inflow valve 45 is occluded.

Figure 6A:
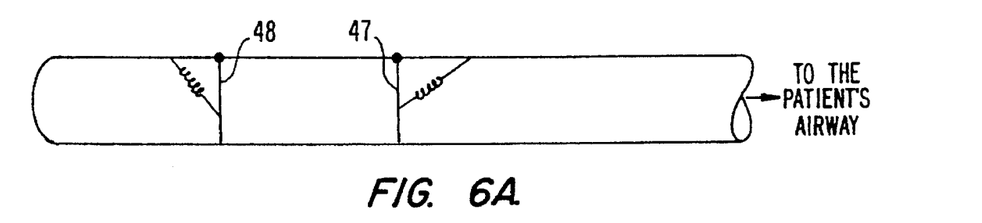
FIG. 6A is a schematic view of a spring biased inflow valve and a spring biased expiration valve to be used in accordance with the present invention.
Figure 6B:
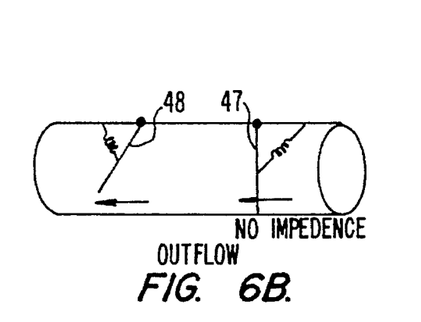
FIG. 6B is a schematic view of FIG. 6A showing the operation of the valves during outflow of air.
Figure 6C:
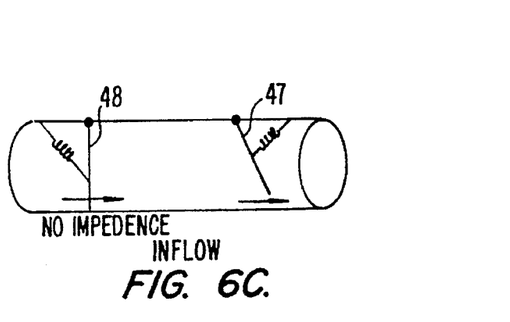
FIG. 6C is a schematic view of FIG. 6A showing the operation of the valves during inflow of air.

FIG. 6A illustrates an inflow valve 47 that is spring biased and an expiration valve 48 that is also spring biased. The inflow valve 47 and the expiration valve 48 are connected in series and may be used in the first alternative embodiment as discussed in connection with FIG. 3, or with the preferred embodiment discussed following in connection with FIG. 9. As shown in FIG. 6C, during the active decompression step, the inflow valve 47 is biased such that it will open when the negative intrathoracic pressure reaches a threshold amount. During the compression phase of ACD-CPR the expiration valve 48 will open to allow air to expire from the patient's lungs when the intrathoracic pressure within the patient's chest reaches a threshold amount as shown in FIG. 6B. Since neither inflow valve 47 nor expiration valve 48 are one-way valves, a fish mouth valve 37 used in connection with a one-way expiration valve 22 as discussed in connection with FIG. 3 must be used. Other valves designed upon a similar principle as the fish mouth valve combination with a one-way expiration valve could also be used. Only one inflow valve 24 and one positive end pressure valve 44 are shown in FIGS. 6A-6C. However, a plurality of inflow valves 47 and/or expiration valves 48 may be connected in a permanent or detachable manner in series to impede the inflow and outflow of air.

Although the valves in FIGS. 6A-6C are shown as being spring-biased, any other valves designed upon a similar principle would work equally as well. The use of such valves as disclosed in FIGS. 6A-6C is only one embodiment and valves constructed according to various other methods and materials is also within the scope of the invention.

Figure 7:
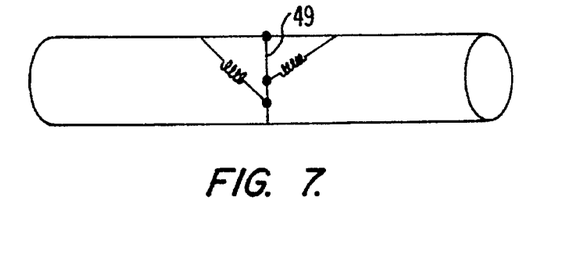
FIG. 7 is a schematic view of a single valve that is spring biased from both sides to be used as an inflow valve and an expiration valve according to the present invention.

As shown in FIG. 7, the inflow valve 47 and the expiration valve 48 may be combined into one joint valve 49 as shown. The joint valve 49 will operate in a manner similar to the two valves 47 and 48 as described in connection with FIG. 6.

Figure 8:
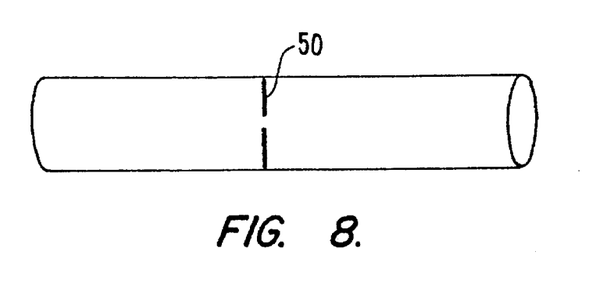
FIG. 8 is a schematic view of a flow restricting orifice to be used with a flow restrictive device according to the present invention.

FIG. 8 illustrates a flow restricting orifice 50 to be used to either impede the air flow into or out of a patient's lungs. The flow restricting orifice 50 operates so that during the decompression step of ACD-CPR air flow is impeded from entering into the patient's lungs, thus increasing the negative intrathoracic pressure. During the compression step, the flow restricting orifice 50 operates to increase the thoracic pressure in the patient's chest by restricting air from exiting from the patient's lungs.

Figure 9:
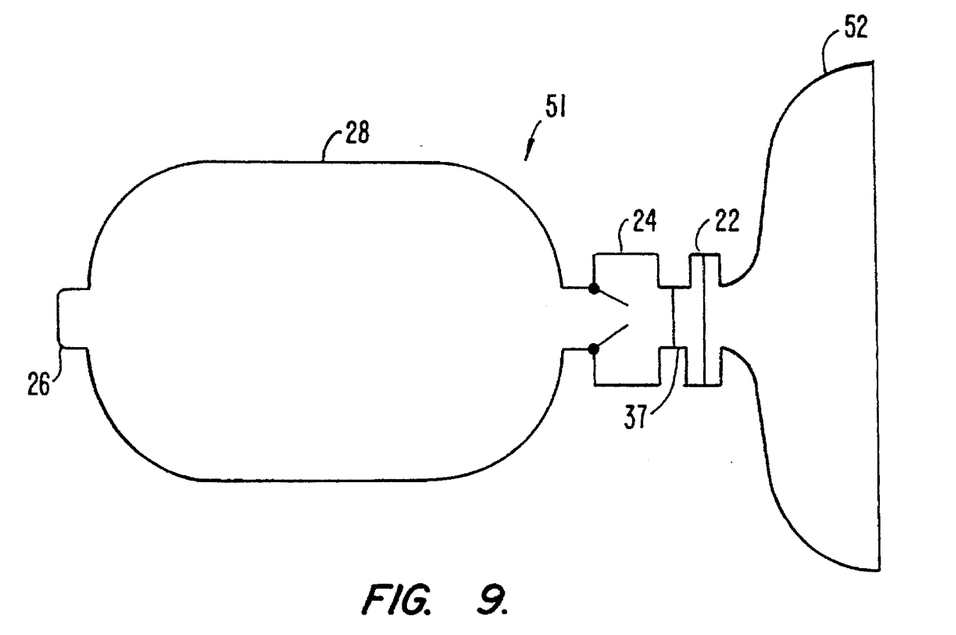
FIG. 9 is a schematic view of an exemplary embodiment of the device for impeding air flow into a patient's lungs according to the present invention.

FIG. 9 illustrates an exemplary embodiment for impeding air flow into a patient's lungs according to the present invention. As shown, the device 51 comprises a ventilation bag 28 that is connected to a facial mask 52 by an inflow valve 24 and an expiration valve 22. Although the facial mask 52 is shown connected to the ventilation bag 28, the facial mask 52 can be used alone or in connection with the ventilation bag. Between the inflow valve 24 and the expiration valve 22 is a one-way fish mouth valve 37 or any other type of one-way valve to prevent air from exiting the patient's lungs and flowing to the ventilation bag 28. The ventilation bag 28 also contains a one-way ventilation valve 26 for allowing air to inflow into the device 51. The exemplary embodiment operates in a manner similar to that of the first alternative embodiment as discussed in connection with FIG. 3. However, instead of inserting an endotracheal tube 36 into the patient's airway, the facial mask 52 is placed over the patient's mouth and nose. A facial strap 54 (not shown) may also be wrapped around the head of the patient to secure the ventilation mask 52 to the patient's face.

Device 51 is preferably used in connection with an oral airway device (not shown) to prevent the patient's airway from becoming occluded, e.g. by the patient's tongue. The oral airway device can be any device that is used to keep the patient's tongue from slipping backward and occluding the airway. Preferably, the oral airway device will be curved and constructed of a plastic material and may or may not be attached to the device 51.

During the decompression phase of ACD-CPR, air is prevented from entering into the patient's lungs through the threshold inflow valve 24 thus increasing the negative intrathoracic pressure. During the compression phase, air is allowed to expire from the patient's lungs through the expiration valve 22. Also, the patient can be ventilated during ACD-CPR by manually squeezing the ventilation bag 28. Consequently, the preferred embodiment serves to enhance cardiopulmonary circulation by increasing the negative intrathoracic pressure to force more blood into the chest from the peripheral venous vasculature.

Figure 10A:
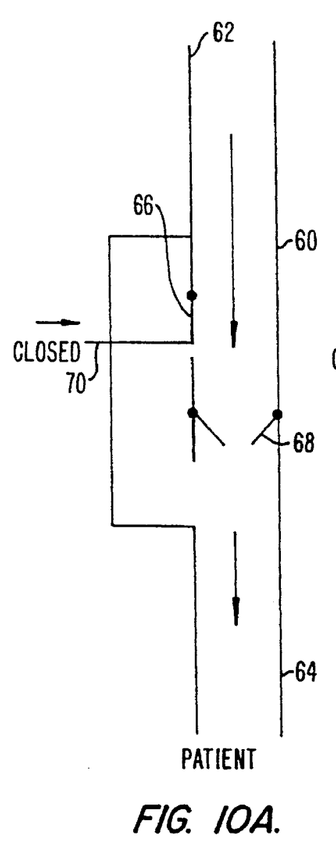
FIGS. 10A–10C are schematic views illustrating another embodiment of the present invention allowing for periodic patient ventilation through a bypassing valve.
Figure 10B:
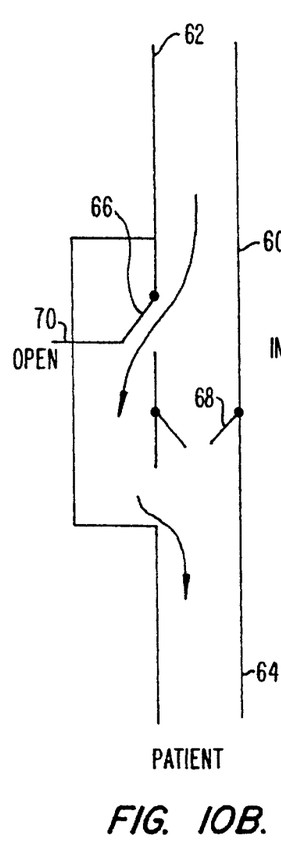
Figure 10C:
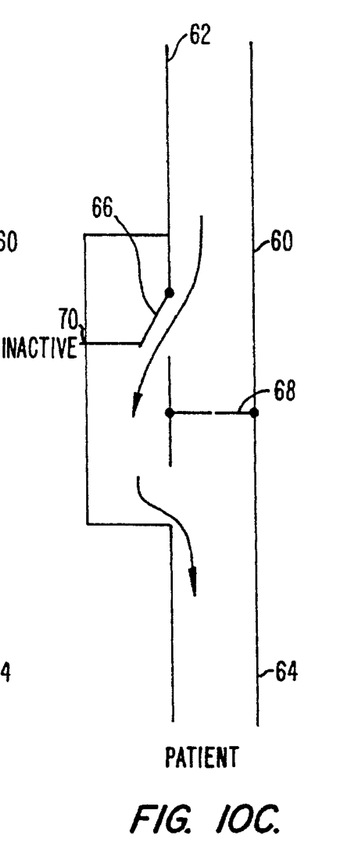

FIGS. 10A-10C show another embodiment of the present invention which allows the patient to be ventilated by bypassing the impeding step. The embodiment comprises a ventilation tube 60 with a proximal end 62 and a distal end 64 that is connected to the patient. The ventilation tube 60 has a one-way bypass valve 66 and a one-way pressure responsive valve 68. The ventilation tube 60 may also have a manual switch 70 attached to the bypass valve 66 and extending through a side of the ventilation tube 60. As shown in FIG. 10A, the switch 70 may be set in a closed position so that the one-way pressure responsive valve 68 opens when the threshold pressure of the valve 68 has been exceeded. At this point, the valve 68 opens allowing for ventilation of the patient. As shown in FIG. 10B, the one-way pressure responsive valve 68 may be bypassed altogether by manually placing the switch 70 in the open position so that the bypass valve 66 is opened allowing air to flow to the patient. FIG. 10C illustrates the operation of the bypass valve 66 with the switch 70 in an inactive mode. Here, the rescuer performing ventilation may do so without added resistance from the impedance step as in FIG. 10A. Instead, bypass valve 66 opens only when the pressure at the proximal end of the tube 62 is greater than atmospheric pressure (0 mmHg), preferably in a range from about 0 mmHg to 5 mmHg. During decompression of the patient's chest, the one-way bypass valve 66 remains closed unless atmospheric pressure is exceeded. Thus, the patient is ventilated only when the rescuer performing ventilation causes the pressure at the proximal end of the tube 62 to exceed atmospheric pressure. The function of the one-way bypass valve 66 may be performed by many different threshold valve designs which are known in the art.

Although the foregoing invention has been described in some detail by way of illustration and example, for purposes of clarity of understanding, it will be obvious that certain changes and modifications may be practiced within the scope of the appended claims.

What is claimed is:

1. A method for increasing cardiopulmonary circulation induced by chest compression and decompression when performing cardio pulmonary resuscitation, by augmenting at least the negative intrathoracic pressure, said method comprising the steps of:

providing a ventilatory tube having a length which extends at least between a patient's mouth and throat, a source of respiratory gases, and at least one inflow valve;

performing chest compression and chest decompression, wherein during chest decompression, said at least one inflow valve prevents respiratory gases from entering the lungs until a negative intrathoracic pressure level is exceeded at which time said at least one inflow valve opens, said at least one inflow valve assisting in increasing the magnitude and duration of negative intrathoracic pressure during decompression and thereby enhancing the amount of venous blood flow into the heart and lungs; and periodically, every 2–10 chest compressions, supplying the patient with gas from the respiratory gas source so as to properly ventilate the patient.

2. The method of claim 1, wherein the negative intrathoracic pressure is in the range from about 0 cm $H_2O$ to $-100$ cm $H_2O$.

3. The method of claim 1, wherein said at least one inflow valve comprises a one-way valve.

4. The method of claim 1, wherein the gas from the respiratory gas source is supplied through the ventilatory tube.

5. The method of claim 1, wherein the decompressing step comprises allowing the patient's chest to expand in response to the chest's resilience.

6. The method of claim 1, wherein the decompressing step comprises lifting or actively expanding the patient's chest to expand the thorax.

7. The method of claim 1, wherein the chest is compressed in the range from about 3.5 cm to 5 cm per compression.

8. The method of claim 1, wherein the chest is compressed in the rate from 60 to 100 per minute.

9. A method for increasing cardiopulmonary circulation induced by chest compression and decompression when performing cardio pulmonary resuscitation, by augmenting at least the negative intrathoracic pressure, said method comprising the steps of:

providing a ventilatory bag which is attached to a facial mask which may be placed on a person's face over the mouth and nose, said mask having at least one inflow valve attached thereto;

performing chest compression and chest decompression, wherein during chest decompression, said at least one inflow valve prevents respiratory gases from entering the lungs until a negative intrathoracic pressure level is exceeded at which time said at least one inflow valve opens, said at least one inflow valve assisting in increasing the magnitude and duration of negative intrathoracic pressure during decompression and thereby enhancing the amount of venous blood flow into the heart and lungs; and periodically, every 2–10 chest compressions, supplying the patient with gas from the respiratory gas source so as to properly ventilate the patient.

10. The method of claim 9, wherein the negative intrathoracic pressure is in the range from about 0 cm $H_2O$ to $-100$ cm $H_2O$.

11. The method of claim 9, wherein said at least one inflow valve comprises a one-way valve.

12. The method of claim 9, wherein the decompressing step comprises allowing the patient's chest to expand in response to the chest's resilience.

13. The method of claim 9, wherein the decompressing step comprises lifting or actively expanding the patient's chest to expand the thorax.

14. The method of claim 9, wherein the chest is compressed in the range from about 3.5 cm to 5 cm per compression.

15. The method of claim 9, wherein the chest is compressed in the rate from 60 to 100 per minute.

16. A method for increasing cardiopulmonary circulation induced by chest compression and decompression when performing cardio pulmonary resuscitation, by augmenting both positive and negative intrathoracic pressures, said method comprising the steps of:

providing a ventilatory tube having a length which extends at least between a patient's mouth and throat, a source of respiratory gases, an exhalation valve, and at least one inflow valve;

performing chest compression and chest decompression, wherein during chest compression, said exhalation valve prevents air from leaving the lungs until a positive intrathoracic pressure threshold is exceeded at which time said exhalation valve opens, said exhalation valve assisting in forcing more blood out of the thorax; and during chest decompression, said at least one inflow valve prevents respiratory gases from entering the lungs until a negative intrathoracic pressure level is exceeded at which time said at least one inflow valve opens, said at least one inflow valve assisting in increasing the magnitude and duration of negative intrathoracic pressure during decompression and thereby enhancing the amount of venous blood flow into the heart and lungs; and periodically, every 2–10 chest compressions, supplying the patient with gas from the respiratory gas source so as to properly ventilate the patient.

17. The method of claim 16, wherein the negative intrathoracic pressure is in the range from about 0 cm H$_2$O to 100 cm H$_2$O.

18. The method of claim 16, wherein the positive intrathoracic pressure is in the range from about 5 cm H$_2$O to 50 cm H$_2$O.

19. The method of claim 16, wherein said at least one inflow valve comprises a one-way valve.

20. The method of claim 16, wherein the gas from the respiratory gas source is supplied through the ventilatory tube.

21. The method of claim 16, wherein the decompressing step comprises allowing the patient's chest to expand in response to the chest's resilience.

22. The method of claim 16, wherein the decompressing step comprises lifting or actively expanding the patient's chest to expand the thorax.

23. The method of claim 16, wherein the chest is compressed in the range from about 3.5 cm to 5 cm per compression.

24. The method of claim 16, wherein the chest is compressed in the rate from 60 to 100 per minute.

25. A method for increasing cardiopulmonary circulation induced by chest compression and decompression when performing cardio pulmonary resuscitation, by augmenting both positive and negative intrathoracic pressures, said method comprising the steps of:

providing a ventilatory bag which is attached to a facial mask which may be placed on a person's face over the mouth and nose, said mask having at least one inflow valve attached thereto, and an exhalation valve;

performing chest compression and chest decompression, wherein during chest compression, said exhalation valve prevents air from leaving the lungs until a positive intrathoracic pressure threshold is exceeded at which time said exhalation valve opens, said exhalation valve assisting in forcing more blood out of the thorax; and during chest decompression, said at least one inflow valve prevents respiratory gases from entering the lungs until a negative intrathoracic pressure level is exceeded at which time said at least one inflow valve opens, said at least one inflow valve assisting in increasing the magnitude and duration of negative intrathoracic pressure during decompression and thereby enhancing the amount of venous blood flow into the heart and lungs; and periodically, every 2–10 chest compressions, supplying the patient with gas from the respiratory gas source so as to properly ventilate the patient.

26. The method of claim 25, wherein the negative intrathoracic pressure is in the range from about 0 cm H$_2$O to 100 cm H$_2$O.

27. The method of claim 25, wherein the positive intrathoracic pressure is in the range from about 5 cm H$_2$O to 50 cm H$_2$O.

28. The method of claim 25, wherein the gas from the respiratory gas source is supplied through the ventilatory tube.

29. The method of claim 25, wherein the decompressing step comprises allowing the patient's chest to expand in response to the chest's resilience.

30. The method of claim 25, wherein the decompressing step comprises lifting or actively expanding the patient's chest to expand the thorax.

31. The method of claim 25, wherein the chest is compressed in the range from about 3.5 cm to 5 cm per compression.

32. The method of claim 25, wherein the chest is compressed in the rate from 60 to 100 per minute.

33. A method for increasing cardiopulmonary circulation induced by chest compression and decompression when performing cardio pulmonary resuscitation, by augmenting at least the negative intrathoracic pressure, said method comprising the steps of:

providing a means for delivering respiratory gases to the lungs, a source of respiratory gases, and at least one inflow valve;

performing chest compression and chest decompression, wherein during chest decompression, said at least one inflow valve remaining closed to prevent any respiratory gases from entering the lungs until a negative intrathoracic pressure level is exceeded at which time said at least one inflow valve opens, said at least one inflow valve assisting in increasing the magnitude and duration of negative intrathoracic pressure during decompression and thereby enhancing the amount of venous blood flow into the heart and lungs; and periodically, every 2–10 chest compressions, supplying the patient with gas from the respiratory gas source so as to properly ventilate the patient.

34. The method of claim 33, wherein the negative intrathoracic pressure is in the range from about 0 cm H$_2$O to −100 cm H$_2$O.

35. The method of claim 33, wherein said at least one inflow valve comprises a one-way valve.

36. The method of claim 33, wherein the decompressing step comprises allowing the patient's chest to expand in response to the chest's resilience.

37. The method of claim 33, wherein the decompressing step comprises lifting or actively expanding the patient's chest to expand the thorax.

38. The method of claim 33, wherein the chest is compressed in the range from about 3.5 cm to 5 cm per compression.

39. The method of claim 33, wherein the chest is compressed in the rate from 60 to 100 per minute.

40. The method of claim 33, wherein the means for delivering gases to the lungs comprises a ventilatory mask.

41. The method of claim 33, wherein the means for delivering gases to the lungs comprises a tube.

* * * * *